(12) United States Patent
Laessig et al.

(10) Patent No.: US 10,656,135 B2
(45) Date of Patent: May 19, 2020

(54) METHOD FOR DETERMINING A MIXING RATIO OF N ORGANIC, MISCIBLE COMPONENTS IN A MIXTURE OF SAID COMPONENTS AND USE OF AN INORGANIC MARKER

(71) Applicant: Bayerische Motoren Werke Aktiengesellschaft, Munich (DE)

(72) Inventors: Daniel Laessig, Schkeuditz (DE); Ines Nikoleizig, Braunsbedra (DE); Florian Hessing, Paderborn (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 101 days.

(21) Appl. No.: 15/937,120

(22) Filed: Mar. 27, 2018

(65) Prior Publication Data

US 2018/0217121 A1 Aug. 2, 2018

Related U.S. Application Data

(63) Continuation of application No. PCT/EP2016/071439, filed on Sep. 12, 2016.

(30) Foreign Application Priority Data

Sep. 28, 2015 (DE) .......... 10 2015 218 600

(51) Int. Cl.
*G01J 3/30* (2006.01)
*G01N 33/44* (2006.01)
(Continued)

(52) U.S. Cl.
CPC ....... *G01N 33/442* (2013.01); *G01N 21/3103* (2013.01); *G01N 21/68* (2013.01)

(58) Field of Classification Search
CPC .. G01N 33/442; G01N 21/3103; G01N 21/68; B65D 81/00; B65D 81/18; B65D 11/50; B65D 51/00
See application file for complete search history.

(56) References Cited

U.S. PATENT DOCUMENTS 4,434,815 A 3/1984 Flaherty et al.
4,478,941 A 10/1984 Hillshafer
(Continued)

FOREIGN PATENT DOCUMENTS

CN 102596539 A 7/2012
DE 44 34 815 A1 4/1996
(Continued)

OTHER PUBLICATIONS

International Search Report (PCT/ISA/210) issued in PCT Application No. PCT/EP2016/071439 dated Nov. 14, 2016 with English translation (five pages).

(Continued)

*Primary Examiner* — Abdullahi Nur
(74) *Attorney, Agent, or Firm* — Crowell & Moring LLP

(57) ABSTRACT

A method for determining a mixing ratio A of n organic, miscible components in a mixture of the components. The method includes the following steps: i) preparing n components in pre-defined quantities, where n is an integer $\geq 2$; ii) mixing a respective inorganic marker with one of the respective components in a pre-defined mixing ratio for each of the respective inorganic markers to the respective component, at least one component being mixed with one inorganic marker, and the inorganic markers being of different chemical natures; iii) producing a mixture of the components; (iv) performing an analysis for the quantitative determination of the quantities of the inorganic markers; and v) determining the mixing ratio A of the n components from the defined quantities of the inorganic markers by means of the pre- (Continued)

defined mixing ratios for each of the respective inorganic markers to the respective component.

12 Claims, 1 Drawing Sheet

(51) Int. Cl.
　　*G01N 21/31*　　　(2006.01)
　　*G01N 21/68*　　　(2006.01)

(56) References Cited

U.S. PATENT DOCUMENTS

| | | | |
|---|---|---|---|
| 2008/0145704 A1* | 6/2008 | Scranton | B01J 20/0229 |
| | | | 428/702 |
| 2010/0108558 A1* | 5/2010 | Zook | C09J 7/00 |
| | | | 206/524.2 |
| 2010/0116517 A1 | 5/2010 | Katzenberger et al. | |
| 2013/0001466 A1 | 1/2013 | Schroeder et al. | |

FOREIGN PATENT DOCUMENTS

| | | |
|---|---|---|
| EP | 1 110 996 A1 | 6/2001 |
| EP | 2 314 442 A1 | 4/2011 |
| WO | WO 86/01818 A1 | 3/1986 |
| WO | WO 2008/098638 A1 | 8/2008 |
| WO | WO 2013/091623 A1 | 6/2013 |
| WO | WO 2013/091623 A8 | 9/2013 |

OTHER PUBLICATIONS

German-language Written Opinion (PCT/ISA/237) issued in PCT Application No. PCT/EP2016/071439 dated Nov. 14, 2016 (six pages).

German-language Search Report issued in counterpart German Application No. 10 2015 218 600.8 dated Aug. 31, 2016 with partial English translation (11 pages).

"Prepregs, Formmassen und Laminate," European Standard, European Committee for Standardization, DIN EN ISO 1172, Dec. 1998, eight (8) pages.

Chinese-language Office Action issued in counterpart Chinese Application No. 201680037481.0 dated Jul. 8, 2019 with English translation (14 pages).

\* cited by examiner

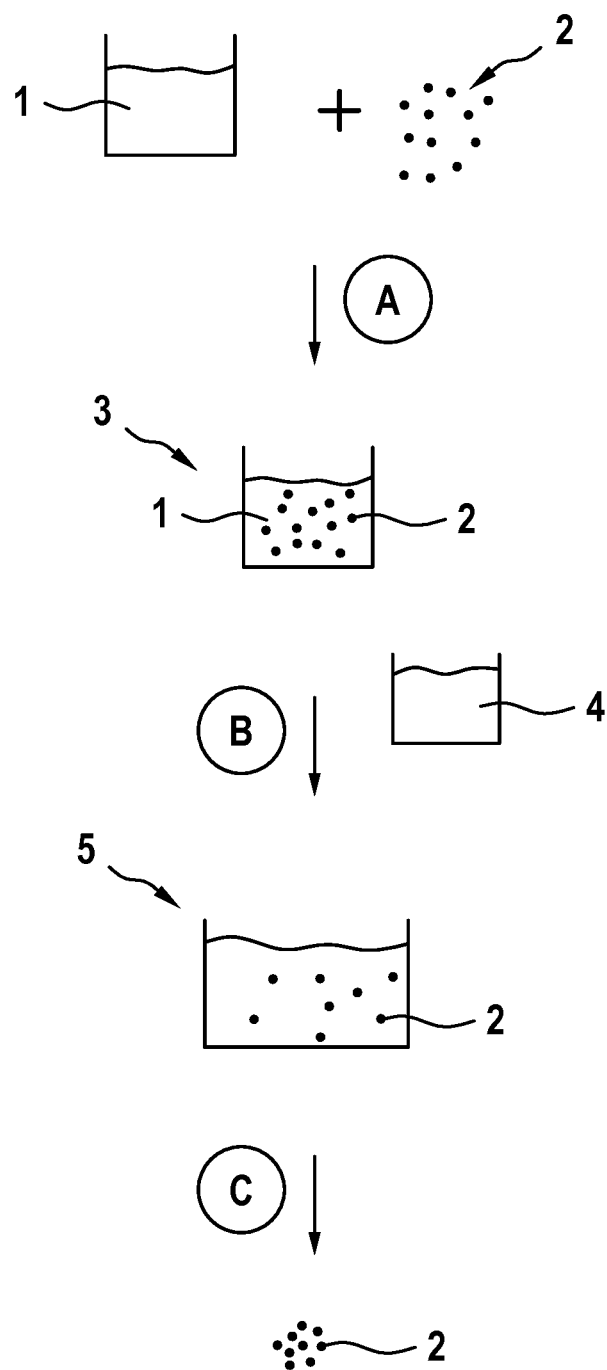

METHOD FOR DETERMINING A MIXING RATIO OF N ORGANIC, MISCIBLE COMPONENTS IN A MIXTURE OF SAID COMPONENTS AND USE OF AN INORGANIC MARKER

CROSS REFERENCE TO RELATED APPLICATIONS

This application is a continuation of PCT International Application No. PCT/EP2016/071439, filed Sep. 12, 2016, which claims priority under 35 U.S.C. § 119 from German Patent Application No. 10 2015 218 600.8, filed Sep. 28, 2015, the entire disclosures of which are herein expressly incorporated by reference.

BACKGROUND AND SUMMARY OF THE INVENTION

The present invention relates to a method for determining a mixing ratio of a number of n organic miscible components in a mixture thereof. The present invention also relates to a method of using an inorganic marker.

Commercially available multicomponent mixtures, for example mousses, foams, sealants and adhesives, once prepared or applied, frequently make it impossible to determine the original mixing ratios between the components. This compromises the qualitative policing of the manufacturing operation for multicomponent mixtures and hinders any attempt to reconstruct the causes of process discrepancies. As a result, mixtures manufactured are incapable of meeting the functional expectations.

Proceeding from this prior art, the present invention addresses the problem of devising a method for determining a mixing ratio of n organic miscible components in a mixture thereof that is technically quick and easy to implement and enables a quantitative analysis of the component quantities originally used for the mixture. The present invention also addresses the problem of devising a use for an inorganic marker.

The problem is solved by a method for determining a mixing ratio A of n organic miscible components in a mixture thereof, comprising the steps of: i) providing n components in predefined amounts, where n is an integer ≥2, ii) mixing respectively one inorganic marker with each one of components respectively in a predefined mixing ratio of the particular inorganic marker to the particular component, wherein at least one component is mixed with one inorganic marker, and wherein the inorganic markers differ in chemical nature, iii) preparing a mixture of the components, iv) performing an analysis to quantitatively determine the amounts of the inorganic markers, and v) determining the mixing ratio A of the n components from the ascertained amounts of the inorganic markers via the particular predefined mixing ratios of the particular inorganic marker to the particular component.

The method of the present invention is applied to mixtures of different organic components which, more particularly, are homogeneously miscible with one another, i.e., form an essentially monophasic mixture. Organic components for the purposes of the present invention are chemical materials or compositions of matter that are or contain functional, active or reactive compounds based essentially on hydrocarbon compounds. Compositions of matter, in addition to hydrocarbon-based compounds, may also contain other organic or inorganic additions such as fillers, pigments, viscosity-regulating substances, antioxidants and the like. These additions do not influence the functionality, activity and/or reactivity of the hydrocarbon-based compounds. The components may further also contain functional additives, for example catalysts. Organic compounds for the purposes of the present invention come with preference from among manufactured polymers or their starting compounds.

The number n of organic miscible components provided according to the present invention is discretional provided n is an integer not less than 2. Each component is mixed with a specific inorganic marker. An inorganic marker is a nonvolatile inorganic compound which is inert with respect to the components and the processing of the components and which does not have a natural origin in the components. A marker is thus an inorganic compound which is typically not present as an additive in the components. Since customary additives are often added to organic components in varying amounts (for example, in the case of viscosity-regulating substances) or merely for technical reasons, as is the case for example with fillers, or alternatively different components contain the same additives (for example the same fillers or pigments), traditionally added additives are not useful as markers for the purposes of the invention. It is not absolutely necessary for all components to be provided a marker; on the contrary, at least those components whose mixing ratio A is to be determined are provided markers. In one embodiment, all components may be provided a marker, so the mixing ratio of any one component to any other component as well as the overall mixing ratio of all components can be determined. In this case, n is the number of markers as well as the number of components.

The particular markers which are mixed with the particular components differ in chemical nature, so their quantities can be quantitatively determined independently of each other. This is a requirement for the later step of the analysis. Once the particular inorganic marker or markers have been mixed with respectively one of the components in respectively a predefined mixing ratio of particular marker to particular component, the components are subsequently processed to afford a mixture. This may be done using commercially available mixing devices, for example a dynamic mixer. The mixture may also contain components that do not include any markers, examples being auxiliary materials, such as solvents and other additives. The amounts thereof do not enter into the A mixing ratio to be determined. The mixture accordingly comprises a homogeneous distribution of all the components and additives added and also of the markers.

This is followed, for example after taking a sample of the mixture or after further processing the mixture, for example after applying the mixture, by a step of performing an analysis to quantitatively determine the amounts of the inorganic markers. The mixture is thus analyzed for ascertaining the amounts of the particular markers. When the marker undergoes a reaction during analysis, the analytical technique is chosen such that the stoichiometry of this reaction is unambiguously known, so the original amount of marker can be deduced.

As a result of the original mixing ratio of any one marker to the particular component mixed with the marker being known, i.e., predefined "marker to component" mixing ratios being present in each case, and by virtue of the fact that the marker is inert and nonvolatile, it is possible to take the corresponding ascertained quantities of marker and deduce therefrom the original quantity of the particular component, from which the mixing ratio A of the components is derivable.

The method of the present invention requires the addition of quantitatively analyzable markers to customarily used components and also the quantitative determination of the markers in a mixture of the components. The technical and time requirements of the method according to the present invention are thus low. The method can be carried out, after sampling, concurrently with the manufacture of products out of the component mixture, making it possible to adjust and re-adjust the manufacturing process and ensure a qualitatively high standard for the products obtained. The method of the present invention provides a simple way to police the mixing ratios of multicomponent systems to assure the functionality and quality of these systems.

In an advantageous development of the method according to the present invention, n-1 components are mixed with respectively one inorganic marker. This means that there are solely n components, all but one being mixed with a marker each. Even though one component does not contain a marker, the amount originally used thereof, and hence the mixing ratio A, is ascertainable from the difference of the ascertained amounts of components having markers via the analyzed "marker to component" mixing ratios. This saves the cost for the marker and reduces the analytical burden while providing equivalent information about the mixing ratio A.

It is advantageous here not to provide a marker to that component which, volumetrically, accounts for the largest share of the mixture of the components. This has been determined to be advantageous for measurement accuracy.

Owing to their high chemical inertness and non-volatility, the inorganic marker is preferably selected from metal oxides and/or metal sulfides. One marker may be used per component, but it is also possible to employ two or more different markers per component, in which case the markers of these components are likewise each chemically different than the markers of the other components.

Very useful markers include oxides or sulfides of the elements copper (Cu), zinc (Zn), iron (Fe), nickel (Ni) and manganese (Mn). Zinc sulfide (ZnS) is a particularly preferred inorganic marker because the quantitative analysis of ZnS is simple to perform and leads to low error rates. ZnS is further sufficiently available in the industrial context and is not toxic and does not cause a health concern.

To save costs as well as substantially reduce impairments to the components regarding their chemical, physical and mechanical properties, another advantageous development is characterized in that a proportion of inorganic marker, based on a combined weight of the respective inorganic marker and the particular component whereto the inorganic marker is added, is less than 5 wt %, preferably from 0.5 to 2 wt %.

In a further embodiment, the present invention provides the step of performing an analysis comprises an ash determination for the mixture as per DIN EN ISO 1172:1998-12 and/or an acid digestion of the mixture. An ash determination is done at temperatures where the functional, active or reactive, essentially hydrocarbon-based compounds of the organic components burn to leave solely inorganic products behind as an ash. Calcination is done to constant weight, so the mixing ratio of the components can be directly deduced from the residue. An acid digestion may be done using aqua regia in particular. This will cause all customary inorganic markers to dissolve. A qualitative analysis of the markers may then be effected by suitable spectroscopic methods provided the spectroscopic method does distinguish between the markers qualitatively. It is thereby possible to perform a precise qualitative analysis of each and every marker even in multicomponent systems having more than two components and more than one marker.

In a further embodiment, the present invention provides that the step of performing the analysis comprises a quantitative determination of the inorganic marker by inductively coupled plasma optical emission spectrometry (ICP-OES), atomic absorption spectroscopy (AAS) or atomic emission spectroscopy (OES). ICP-OES, also known as ICP-AES or ICP plasma spectroscopy, is an optical emission spectroscopy featuring inductively coupled plasma (ICP) as excitation source, which offers ease of handling, high sensitivity and precision and also a relative freedom from interferences. It enables qualitative and quantitative analysis of the marker at one and the same time, so every component can be assigned a corresponding amount of marker.

It is further advantageous for the organic miscible component to be selected from thermoplastics, thermosets, elastomers and their starting compounds, e.g., the monomers used. These organic compounds are extensively used in multicomponent systems and functional products, so the determination of the mixing ratio of their starting components is very germane. It is preferable for these organic components to include particularly polyurethanes, epoxides, polyacrylates, polyamides, polyolefins and mixtures thereof.

The method of the present invention is further applied with advantage to a mixture that is an adhesive, a sealant or a foam. Particularly these homogeneous mixtures have a high level of functionality, the quality of which by determining the mixing ratio A is of essential significance.

The present invention likewise provides the method of using an inorganic marker for determining a mixing ratio of components in multicomponent mixtures such as foam, adhesive and sealant materials. ZnS is particularly useful as the marker.

Other objects, advantages and novel features of the present invention will become apparent from the following detailed description of one or more preferred embodiments when considered in conjunction with the accompanying drawings.

BRIEF DESCRIPTION OF THE DRAWING

FIG. 1 shows a schematic process flow diagram for the method of the present invention in an advantageous further development.

DETAILED DESCRIPTION OF THE DRAWING

The present invention is elucidated in detail with reference to a working example. FIG. 1 only depicts those aspects of the method according to the present invention which are of interest here, all other aspects being omitted for clarity.

What FIG. 1 shows in detail is the simplest form of the method which the present invention provides for determining a mixing ratio A of organic miscible components in a mixture thereof. The process of preparing a mixture 5 from two components 1 and 4 is described, although only one of the components, namely a first component 1, comprises an inorganic marker 2. The first step comprises providing the first organic component 1. The first organic component may be, for example, a thermoplastic, a thermoset, an elastomer or a starting compound for these manufactured polymers, such as a monomer. The first component 1 is mixed with an inorganic marker 2 in step A. The inorganic marker 2 is an inert nonvolatile compound which reacts neither with the first component 1 nor with the subsequently to-be-added second component 4 and also does not react or volatilize under the processing conditions of components 1 and 4. The inorganic marker 2 is mixed with the first organic component 1 in a certain "marker to first component 1" mixing ratio. This means that the starting weights of first component 1 and inorganic marker 2 are known. The mixture obtained is a mixture 3 of first organic component 1 and inorganic marker 2. Marker 2 and first component 1 are homogeneously distributed in one another in the mixture.

The second component 4 is provided separately. Method step B comprises preparing a mixture 5 of the first organic component 1 (comprising marker 2) and of the second organic component 4. As a result of the first organic component 1 and the second organic component 4 being miscible with one another, the mixture 5 comprises a homogeneous distribution of the first component 1, of the second component 4 and of the marker 2.

Method step C comprises performing an analysis to quantitatively determine the amounts of inorganic marker 2 in mixture 5, for example after applying said mixture 5. This may be done for example by ash determination for mixture 5 as per DIN ISO 1172: 1998-12. Alternatively, the mixture 5 may be subjected to an acid digestion with aqua regia and the resulting solution containing the dissolved marker 2 analyzed, for example by ICP-OES, and the level of marker 2 quantitatively determined. The marker 2 quantity thus ascertained can be used to deduce the original amount of first component 1 via the predefined "marker 2 to first component 1" mixing ratio and the mixing ratio A of the first organic component 1 to the second organic component 4 via the total weight of mixture 5.

The method works with any desired number n components where n≥2, subject to the proviso that chemically different inorganic markers are provided at least for n-1 components and one specific marker is added to one specific component before the step of forming the mixture from the components. The amounts of all markers are then determined separately in method step C. The "marker to component" ratio predefined for every marker can be used to deduce the originally used amount of the particular component used and hence the mixing ratio A of the components to each other.

The preceding description of the present invention serves solely for illustrative purposes and not for the purpose of restricting the invention. Various changes and modifications are possible within the context of the invention without going outside the scope of the invention and also of its equivalents.

LIST OF REFERENCE SIGNS

1 first organic component
2 inorganic marker
3 mixture of first organic component and inorganic marker
4 second organic component
5 mixture of first organic component and second organic component The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for determining a mixing ratio A of n organic miscible components in a mixture thereof, comprising the steps of:
providing n components in predefined amounts, where n is an integer ≥2;
mixing one inorganic marker with each one of the components respectively, in a predefined mixing ratio of a particular inorganic marker to a particular component, wherein at least one component is mixed with one inorganic marker, and wherein the inorganic markers differ in chemical nature;
preparing a mixture of the components;
performing an analysis to quantitatively determine the amounts of the inorganic markers; and
determining the mixing ratio A of the n components from the determined amounts of the inorganic markers using the particular predefined mixing ratios of the particular inorganic marker to the particular component.

2. The method according to claim 1, wherein n-1 components are mixed with respectively one inorganic marker.

3. The method according to claim 1, wherein the inorganic marker is selected from metal oxides and/or metal sulfides.

4. The method according to claim 3, wherein the inorganic marker is ZnS.

5. The method according to claim 1, wherein a proportion of inorganic marker, based on a combined weight of the inorganic marker and the particular component to which the inorganic marker is added, is less than 5 wt%.

6. The method according to claim 1, wherein a proportion of inorganic marker, based on a combined weight of the inorganic marker and the particular component to which the inorganic marker is added, is from 0.5 to 2 wt%.

7. The method according to claim 1, wherein the step of performing an analysis comprises an ash determination for the mixture and/or an acid digestion of the mixture.

8. The method according to claim 1, wherein the step of performing an analysis comprises a quantitative determination of the inorganic marker by atomic absorption spectroscopy or atomic emission spectroscopy.

9. The method according to claim 1, wherein the organic miscible components are selected from the group consisting of thermoplastics, thermosets and elastomers and their starting compounds.

10. The method according to claim 1, wherein the organic miscible components are selected from the group consisting of polyurethanes, epoxides, polyimides, polyacrylates, polyamides, polyolefins and mixtures thereof.

11. The method according to claim 1, wherein the mixture is an adhesive, a sealant or a foam.

12. A method of determining a mixing ratio of components in multicomponent mixtures using an inorganic marker comprising the step of performing an analysis that includes a quantitative determination of the inorganic marker by inductively coupled plasma optical emission spectrometry, atomic absorption spectroscopy or atomic emission spectroscopy, wherein the inorganic marker is ZnS and the multicomponent mixtures are foams, adhesives or sealant materials.

* * * * *